United States Patent [19]
Behan et al.

[11] Patent Number: 5,711,941
[45] Date of Patent: Jan. 27, 1998

[54] PERFUMED UNDERARM HYGIENE PRODUCTS

[75] Inventors: John Martin Behan, Ashford; Richard Arthur Birch, Hythe; Kathleen Mary Tuck, Ashford, all of Great Britain

[73] Assignee: Unilever Patent Holdings, B.V., Rotterdam, Netherlands

[21] Appl. No.: 705,909

[22] Filed: Aug. 29, 1996

Related U.S. Application Data

[63] Continuation of Ser. No. 773,331, Oct. 11, 1991, abandoned.

[30] Foreign Application Priority Data

Oct. 11, 1990 [GB] United Kingdom ............... 9022147

[51] Int. Cl.$^6$ ............... A61K 7/32; A61K 7/00
[52] U.S. Cl. ............... 424/65; 424/400; 424/401; 424/DIG. 5; 512/1
[58] Field of Search ............... 424/400, 401, 424/65; 512/1

[56] References Cited

U.S. PATENT DOCUMENTS 5,089,269  2/1992  Noda et al. ............... 424/401

FOREIGN PATENT DOCUMENTS

| A 201134 | 11/1986 | European Pat. Off. ............... 424/65 |
| A2 279328 | 8/1988 | European Pat. Off. ............... 424/65 |
| 303461 | 7/1989 | European Pat. Off. ............... 424/65 |
| A2 384034 | 8/1990 | European Pat. Off. ............... 424/65 |
| 1275969 | 6/1972 | United Kingdom ............... 424/65 |

OTHER PUBLICATIONS

J. M. Millen, B.A., B. M. Mitzner, M.S., J. Brenner, Ph.D., & E. H. Polak, M.S., Encapsulated Pefumes in Aerosol Products, Journal of the Society of Cosmetic Chemists, vol. 22, Sep. 1971, pp. 652–666.

*Primary Examiner*—Shelley A. Dodson
*Attorney, Agent, or Firm*—Cushman Darby & Cushman IP Group Pillsbury Madison & Sutro LLP

[57] ABSTRACT

The invention concerns perfumed underarm hygiene products containing perfume encapsulated in a film forming encapsulation material showing improved re-encapsulating properties as evidenced by the "perfume re-encapsulation test. The underarm hygiene products preferably contain 0.05–10% w/w of perfume encapsulates. The perfume encapsulates used contain preferably 15–65% w/w of perfume. The underarm hygiene products may additionally contain a quantity of neat perfume.

5 Claims, 2 Drawing Sheets

PERFUMED UNDERARM HYGIENE PRODUCTS

This is a continuation of application No. 07/773,331, filed on Oct. 11, 1991, abandoned.

The present invention concerns perfumed underarm hygiene products. These products are used to control underarm perspiration and production of malodours during periods of physical exertion or stress. More specifically the present invention concerns perfume encapsulates for incorporation in anhydrous underarm hygiene products which enable the perfume to be released during periods of perspiration. Furthermore the perfume is re-encapsulated on the skin when perspiration stops and the skin dries, so that on each subsequent cycle of perspiration and drying perfume is released and re-encapsulated until all the perfume is exhausted.

Underarm hygiene products are commonly sold as aerosol, dry stick, roll-on, or pump spray. They may contain a metal salt to control perspiration and often they contain alcohol (usually ethanol) to control bacterial growth and thus reduce the formation of malodours. Perfume is usually present to mask any malodours which may be produced and to provide a pleasing fragrance to the skin. The metal salts are a hostile environment for many perfume components and cause them to degrade prior to application on the skin.

The perfume may be protected from the hostile environment within the product by encapsulation in a substrate which is insoluble in the product base. The substrate must be soluble in water to allow release of the perfume during perspiration. Such products are described in GB 1 275 969 and EP 303 461. Perfume which has been processed as described therein is known as perfume encapsulate. A perfume encapsulate is defined for the purposes of this invention as a solid matrix of film-forming substrate, containing droplets of perfume.

Perfume is by nature a mixture of components with various volatilities. When put on the skin the more volatile components are present for a limited period, particularly under hot and humid conditions. If the perfume can be encapsulated in a solid matrix such that it can be released only when required, then the period over which the perfume is perceived may be extended. Such a product has been described in EP 279 328 wherein the perfume is encapsulated in a form such that the perfume may be released by perspiration. In that patent application the perfume is combined with a water-soluble film-forming substrate and an emulsifying agent. An additional benefit described in EP 279 328 is reversible re-encapsulation i.e. when the skin dries the residual perfume is re-encapsulated by the combination of film-forming substrate and emulsifying agent, to be released again on subsequent wetting. A similar system, based on encapsulated perfumes is described in J. Soc. Cosmet. Chem., 22 (1971), pp. 655–666.

The advantages of encapsulating a perfume as above are:
1) perfume is protected from degradation by hostile base components (e.g. metal salts)
2) perfume is retained until needed (i.e. until perspiration occurs)
3) perfume is re-encapsulated when perspiration stops and is retained until further perspiration occurs.

It is an object of the present invention to provide improved underarm hygiene products containing perfume encapsulates from which the perfume is released by perspiration. It is another object of the invention to provide perfume encapsulates having improved re-encapsulating properties to those described in the prior art above. The encapsulation material is a self-emulsifying film-forming substrate which emulsifies the perfume in water without the necessity for additional emulsifying agent. The possible advantages of these perfume encapsulates are:
1. simpler formulations compared to the prior art referred to above;
2. more convenient processing;
3. higher perfume loading.

The high perfume loading leads to a number of additional advantages:
a) less film-forming substrate is required
b) the product is cheaper
c) less film-forming substrate is left on the skin and the product is more consumer acceptable
d) a smaller quantity of solid perfume encapsulate is required in the underarm hygiene product and less opportunity arises for blockage of an aerosol nozzle if the product is an aerosol
e) a smaller quantity of solid perfume encapsulate is required in the product which leads to easier mixing and dispersion
f) less solid material is required to be handled and stored Finally, it is an object of the invention to provide a process for producing underarm hygiene products by incorporating therein improved perfume encapsulates.

Certain starches, waxy starches, modified starches, and modified waxy starches are self-emulsifying film-forming substrates are suitable as encapsulation materials. They will emulsify perfume in water, will form a film on drying, will release perfume and re-encapsulate it again after rewetting and drying, and in addition are suitable for use in cosmetics and toiletries. The use of self-emulsifying encapsulation materials obviates the need to add additional emulsifying agents and the encapsulates preferably do not contain such emulsifying agents. It has been found that superior underarm hygiene products are obtained if the perfume encapsulates used therein are such that the product passes the test criteria hereinafter described under "Perfume re-encapsulation test".

Specifically, encapsulation media which have optimal properties for use in perfume encapsulates in underarm hygiene products, are N-Lok and Purity Gum BE (Trade names), both supplied by National Starch and Chemical Company (NSCC).

As used herein the term "perfume" denotes one or a mixture of perfume components, optionally mixed with a suitable solvent, diluent or carrier, which is used to impart a desired odour to the underarm hygiene product itself and to the skin of the person using it.

Perfume components and mixtures thereof which can be used for the preparation of such perfumes may be natural products such as essential oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenyl-carbinyl acetate, p-tert.butyl-cyclohexyl acetate, isononyl acetate, vetiveryl acetate, vetiverol, alpha-n-amylcinammic aidehyde, alphahexylcinammic aldehyde, 2-methyl-3-(p-tert.butylphenyl)-propanol, 2-methyl-3-(p-isopropylphenyl)-propanal, 3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyltetrahydropyran, methyldihydrojasmonate, 2-n-heptylcyclopentanone, 3-methyl-2-pentylcyclopentanone, n-decanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylionones, irones, cis-3-hexenol and esters thereof, indane musk fragrances, tetralin musk fragrances, isochroman musk fragrances, macrocyclic ketones, macrolactone musk frangrances, ethylene brassylate, aromatic nitro-musk fragrances.

Suitable solvents, diluents or carriers for perfumes as mentioned above are for example: ethanol, isopropanol, diethylene glycol monoethyl ether, dipropylene glycol, diethyl phthalate, triethyl citrate, etc.

To prepare the perfume encapsulate the self-emulsifying film-forming substrate is first dispersed in water. The solids content of this dispersion may be between 10% and 65% by weight, preferably between 20% and 50%. Both N-Lok and Purity Gum BE are supplied as "cold water soluble" starches, however, both benefit from a "cooking" procedure, i.e. the dispersion should be stirred at 80° C. for thirty minutes. The perfume is then added (after cooling the dispersion to below 45° C.) and mixed, using a high shear mixer if necessary to obtain complete emulsification. The proportion of perfume in the mixture should be sufficient to provide the required perfume level in the final dry encapsulate particles, which may be between 15% and 65%, preferably between 20% and 50%. Particulate encapsulates may be obtained by spray-drying the emulsion using ordinary spray-drying techniques.

The perfume encapsulate may be added to underarm hygiene products, such as aerosols, dry sticks, roll-ons, or pump-sprays by mixing during the manufacture of the product. In some cases the emulsion itself can be used. The weight proportion of perfume encapsulate in the product may be between 0.05% and 10%, preferably between 0.5% and 2.5% and the product may also contain neat perfume in a weight proportion between 0% and 5%, preferably between 0.1% and 2.5% w/w. The neat perfume may be the same or a different perfume as that which is used in encapsulated form. Generally, the amount of neat perfume in an underarm hygiene product according to the invention will be lower than the amount of encapsulated perfume in that product.

During storage of the product the encapsulated perfume is protected from degradation by hostile base ingredients e.g. metal salts, and from losses by evaporation. When the product is applied to the skin the perfume is retained in encapsulated form, any free perfume which has additionally been incorporated in the product providing the initial fragrance impact usually required of these products. The encapsulated perfume is retained in encapsulated form for an extended period, usually 24 hours or longer, or until the wearer begins to perspire. As the wearer perspires the moisture reforms the perfume emulsion from the perfume encapsulate and releases perfume into the atmosphere. When the wearer cools and perspiration ceases the moisture evaporates and the self-emulsifying film-forming substrate forms a film on the skin which re-encapsulates any remaining perfume and retains it within the film. Perfume is retained within the film until a second or subsequent period of perspiration occurs, the emulsion is then reformed and the perfume is released again. This cycle of perfume release and re-encapsulation may occur a number of occasions until the perfume is exhausted.

The properties of the self-emulsifying film-forming substrate should be such that the perfume encapsulate provides the triple benefits of 1) perfume protection in the product, 2) perspiration activated fragrance boost, and 3) re-encapsulation of perfume on the skin, but in addition the appearance and tactile properties of the perfume encapsulate when applied to the skin as part of an underarm hygiene product must be acceptable to the consumer. When re-encapsulation takes place the film formed on the skin must have the appropriate properties for cosmetic or toiletry use e.g. it must not be tacky, it must be invisible, it must be odourless or of pleasing odour. N-Lok and Purity Gum BE have been found to meet all the above criteria.

BRIEF DESCRIPTION OF THE DRAWINGS

The invention is described by reference to the accompanying drawings wherein.

Perfume Re-encapsulation Test

Figure 1:
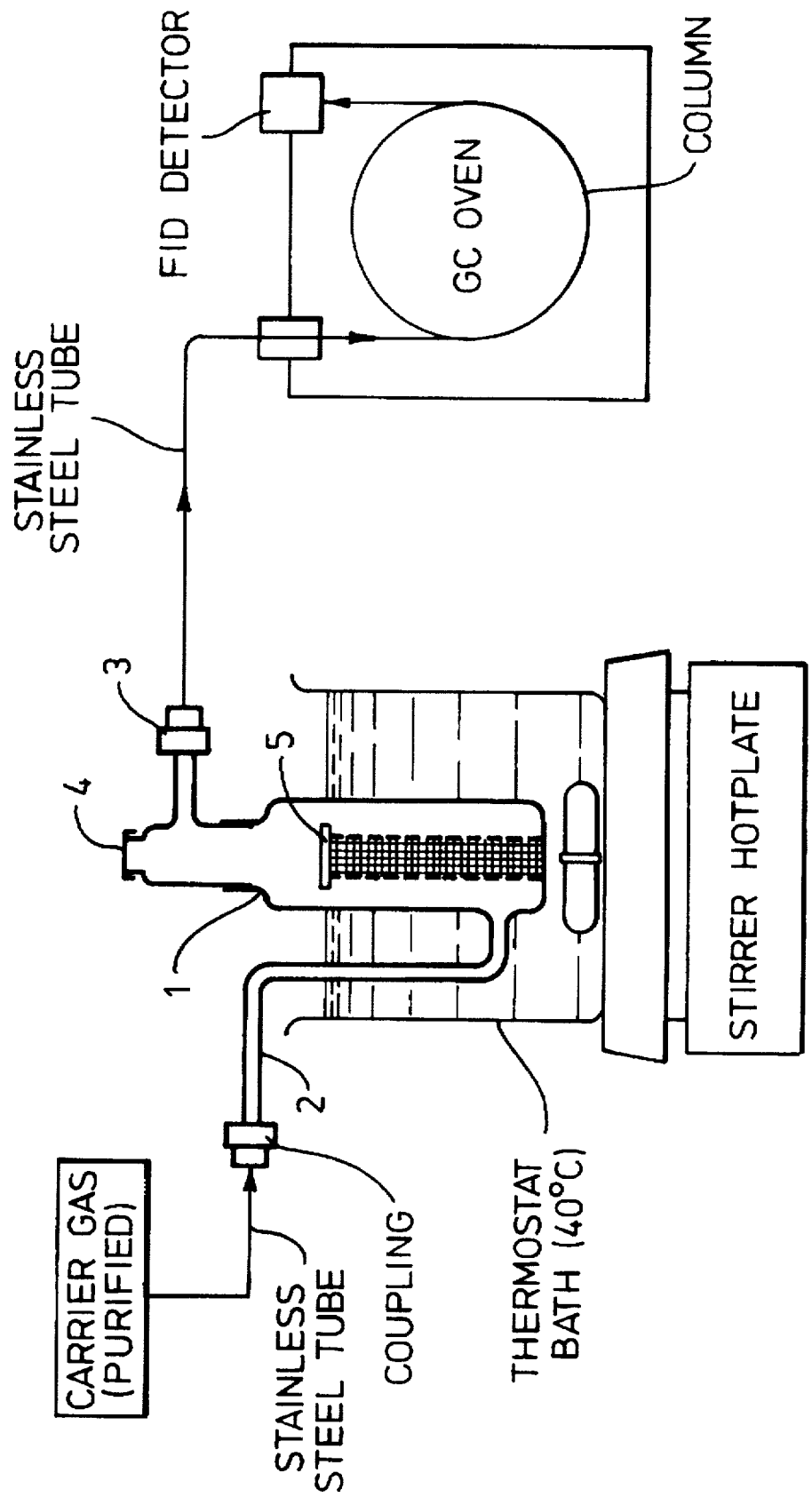
FIG. 1 illustrates apparatus used for testing the reencapsulation properties of perfume encapsulates.

The following in vitro test demonstrates the re-encapsulation properties of perfume encapsulates. The test uses a headspace trapping technique combined with gas chromatography to quantify the amount of perfume in the atmosphere above the product sample. The apparatus (Dynamic headspace sampling apparatus shown in FIG. 1) consists of a glass tube (1) with an inlet (2) for clean inert carrier gas (nitrogen) at the bottom, an outlet (3) for carrier gas and evaporated perfume at the upper side and a septum (4) at the top end; inside the tube on the bottom is a stainless steel wire mesh support (5) for polycotton discs; the apparatus is supported in a water bath maintained at 40° C. Once the carrier gas passed through the apparatus carrying with it the perfume released from the polycotton discs, it passes through a gc column (Stationary phase: Tenax Tex., 30 cm long, 6 mm diameter) connected to a flame ionisation detector (FID).

A disc (1.7 cm diameter) of polycotton is used for the test substrate. The disc is first washed in distilled water, and dried at 100° C. prior to use. The product containing either free perfume or perfume encapsulate is then applied to the polycotton disc. Any interfering volatile matter is removed by placing the disc in an oven at 40° C. for one hour. The disc is then placed in the apparatus (product side down), and the apparatus closed.

Figure 2:
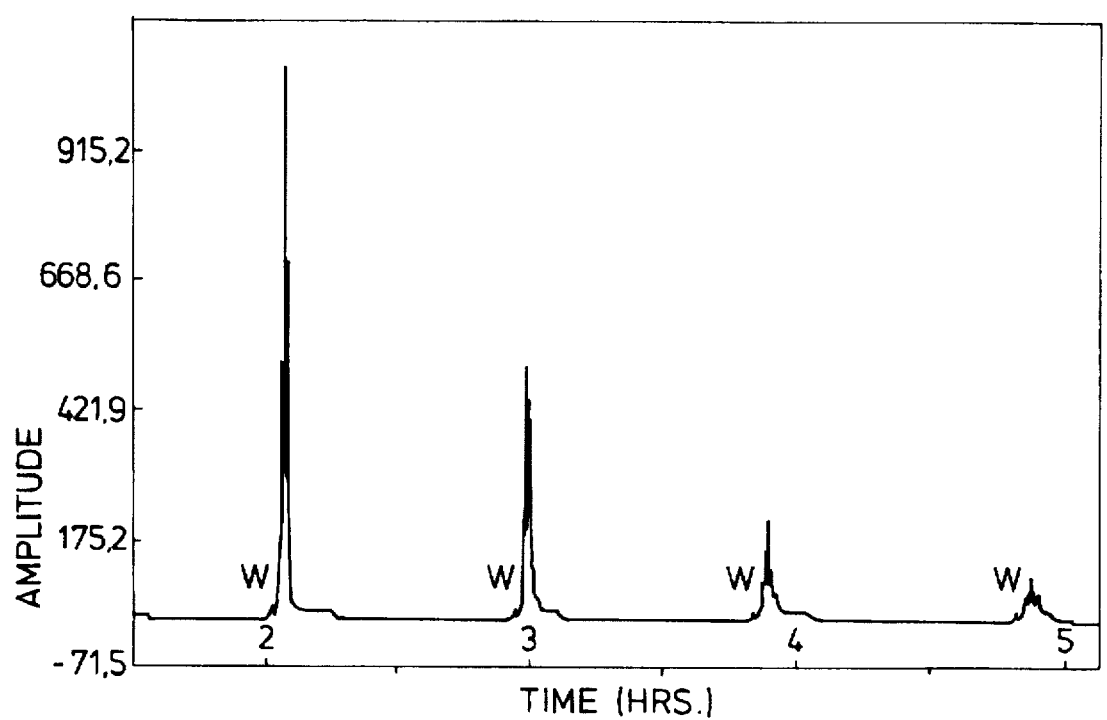
FIG. 2 is a graph showing the monitored and integrated response of perfume ingredients after periodic re-wetting.

The carrier gas is passed through the apparatus at 50 ml/minute with the gc oven at 25° C. A syringe is inserted through the rubber septum and 10 microliters of distilled water dropped onto the disc. After 30 minutes, the gc oven temperature is raised to 250° C. as quickly as possible. The response of the perfumery ingredients on the FID is monitored and integrated (FIG. 2). The sample is periodically re-wetted using the syringe as before and the similar process repeated to obtain the integrated response for the perfume ingredients after each re-wetting.

Some perfume would generally be expected to be retained to a second wetting, though not to the extent of the encapsulates according to the invention. For a perfume encapsulate to show true re-encapsulating behaviour, the integrated perfume areas must satisfy the following criteria:

1. The ratio of the gc integrated areas from the underarm hygiene product containing perfume encapsulate and the underarm hygiene product containing an equivalent amount of the respective free perfume must be at least 6 at the first wetting, 4 at the second wetting and 2 at the third wetting.

2. For any underarm hygiene product containing perfume encapsulate the ratio of the gc integrated area at the first wetting to the integrated area at the second wetting must be less than 2.

The invention is illustrated by the following examples but not in any way limited thereto.

EXAMPLE 1: Preparation of perfume encapsulate

Step 1: The self-emulsifying film-forming substrate (N-Lok, 90 parts) was dispersed in cold water (225 parts) with stirring.

Step 2 (optional): The mixture was then heated, with continuous stirring, to 80° C. and maintained at this temperature, with continuous stirring for 30 minutes. (NB. N-Lok is supplied by NSCC as "Cold water soluble" starch, however it benefits from a "cooking" procedure).

Step 3: The perfume oil (60 parts) was added (after cooling the dispersion to 45° C.) with high shear mixing.

Step 4: The resulting emulsion was spray-dried to form the perfume encapsulate. A commercial spray-dryer was used, i.e. "Production Minor" of Niro, Denmark, using a rotary disc atomiser. The drying conditions were as follows:

Inlet temperature: 220° C.

Outlet temperature: 95° C.

Disc speed: 12,000 rpm

Emulsion feed rate: Adjusted to maintain the outlet temperature constant

EXAMPLE 2: Formulations of underarm products

|  | a % w/w | b % w/w |
|---|---|---|
| a) Aerosol |  |  |
| Aluminium chlorhydrate | 7.0 | 7.0 |
| Isopropyl myristate | 10.0 | 10.0 |
| Aerosil 200 (Degussa) | 0.6 | 0.6 |
| Eutanol G (Henkel) | 3.0 | 3.0 |
| Silicone DC344 (Dow Corning) | 10.8 | 10.8 |
| Irgasan DP300 (Ciba Geigy) | 0.1 | 0.1 |
| Perfume | 0.5 | — |
| Perfume encapsulate | — | 1.25 |
| Hydrocarbon propellant | 68.0 | 67.25 |
| b) Dry-stick: |  |  |
| Rezal 36GP (Reheis Chem.) | 20 | 20 |
| Stearyl alcohol | 20 | 20 |
| Arlacel 165 (ICI) | 1 | 1 |
| PEG400 distearate | 1 | 1 |
| Talc (Whittaker, Clark & Daniels) | 1 | 1 |
| Breox PEG 1000 (BP) | 5 | 5 |
| Aerosil 200 (Degussa) | 1.5 | 1.5 |
| Dow Corning Fluid DC345 | 49.5 | 48.0 |
| Perfume | 1.0 | — |
| Perfume encapsulate | — | 2.5 |

-continued

|  | a % w/w | b % w/w |
|---|---|---|
| c) Roll-on |  |  |
| Bentone gel IPM (NL Industries) | 27.0 | 27.0 |
| Silicone fluid DC344 (Dow Corning) | 52.0 | 50.5 |
| Aluminium Chlorohydrate powder | 20.0 | 20.0 |
| Perfume | 1.0 | — |
| Perfume encapsulate | — | 2.5 |

EXAMPLE 3: Olfactory assessment of the invention

Products were produced as in Example 2, containing either neat perfume or perfume encapsulate. Capsul (Trade mark NSCC) was included in the test. Capsul is a self-emulsifying starch, typical of the prior art, which can be used without emulsifier but which does not exhibit significant re-encapsulation properties. The products were applied to a paper card and allowed to dry out (one hour at ambient temperature). The odours of each card were then assessed by experts. Water was applied to the cards from a spray and after one minute the cards were re-assessed by the same experts. The cards were allowed to dry for 24 hours and then re-assessed after the application of a second water spray. The results were:

|  | Change in odour intensity on wetting | |
|---|---|---|
| Encapsulating material | initial | 24 hours |
| a) Aerosol: |  |  |
| neat perfume | 0* | −2 |
| N-Lok | 2 | 2 |
| Purity Gum BE | 0 | 2 |
| Capsul | −1 | 0 |
| b) Dry-stick: |  |  |
| neat perfume | 0 | 0 |
| N-Lok | 1 | 3 |
| Purity Gum BE | 0 | 2 |
| Capsul | 0 | 0 |

Key to the tables:
3 Very large increase in odour intensity
2 Large increase in odour intensity
1 Moderate increase in odour intensity
0 No change in odour intensity
−1 Moderate decrease in odour intensity
−2 Large decrease in odour intensity The odour assessments demonstrate that no fragrance boost (increase in fragrance intensity) is observed when the samples prepared with free perfume are wetted, either initially or after 24 hours. Similarly, no fragrance boost is observed when the samples containing a perfume encapsulate prepared with Capsul are wetted, either initially or after 24 hours. However, a strong fragrance boost is observed when samples containing perfume encapsulates prepared with N-Lok or Purity Gum BE are wetted. The effect is observed after storing the dry cards for 24 hours at room temperature, demonstrating that the perfume is retained on the surface until released by water and is then re-encapsulated and retained until further wetting occurs.

EXAMPLE 4: Results of the Perfume re-encapsulation test

The test results for the performance of dry-stick antiperspirants containing either neat perfume, perfume encapsulated in N-lok or perfume encapsulated in Capsul are as follows:

| GC Integrated area (arbitrary units) | | | |
|---|---|---|---|
| Wetting times | Neat perfume | N-Lok | Capsul |
| 1 | 845 | 5922 | 6027 |
| 2 | 722 | 3594 | 1803 |
| 3 | 720 | 1733 | 916 |
| 4 | — | 855 | 671 |
| Test ratio 1: | | Perfume encapsulated/neat | |
| 1st wetting | | 7.0 | 7.1 |
| 2nd wetting | | 5.0 | 2.5 |
| 3rd wetting | | 2.4 | 1.3 |
| Test ratio 2: | | Perfume encapsulate peak 1/peak 2 | |
| | | 1.6 | 3.3 |

We claim:

1. A perfumed underarm hygiene product comprising 0.05–10% w/w of perfume encapsulates containing 15–65% w/w perfume encapsulated by a self-emulsifying film-forming encapsulation material, which encapsulates the perfume without the addition of an emulsifying agent, said encapsulates being such that they release said perfume on wetting by perspiration but re-encapsulate on drying after release of perfume, said perfumed underarm hygiene product, when compared with a similar perfumed underarm hygiene product containing an equivalent amount of free perfume of identical composition as the perfume in the perfume encapsulate, satisfying the following criteria:
  a) the ratio of the gas chromatography integrated areas from the underarm hygiene product containing the perfume encapsulates to the underarm hygiene product containing the free perfume is at least 6 at a first wetting, at least 4 at a second wetting and at least 2 at a third wetting; and
  b) the ratio of the gas chromatography integrated area of the underarm hygiene product containing the perfume encapsulates at a first wetting to the gas chromatography integrated area at a second wetting of the same material, is less than 2.

2. A perfumed underarm hygiene product according to claim 1, further comprising up to 5% w/w of free non-encapsulated perfume.

3. A perfumed underarm hygiene product according to claim 1 which does not contain an additional emulsifying agent.

4. A perfumed underarm hygiene product according to claim 1 wherein the encapsulation material is a cold water starch which has been heated up to 80° C. and then cooled to below 45° C., after which the perfume is added, followed by mixing to form an emulsion and then spray drying the emulsion.

5. A perfumed underarm hygiene product according to claim 1 which is an aerosol, a dry stick, a roll-on or a pump spray.

* * * * *